US00PP17268P2

(12) United States Plant Patent
Field

(10) Patent No.: US PP17,268 P2
(45) Date of Patent: Dec. 12, 2006

(54) APPLE TREE NAMED 'MAHANA RED BRAEBURN'

(50) Latin Name: *Malus Mill.*
Varietal Denomination: Mahana Red Braeburn

(76) Inventor: Robin T. Field, Old Coach Road, R.D. 1, Upper Moutere, Nelson (NZ)

( * ) Notice: Subject to any disclaimer, the term of this patent is extended or adjusted under 35 U.S.C. 154(b) by 0 days.

(21) Appl. No.: 11/082,145

(22) Filed: Mar. 16, 2005

Related U.S. Application Data

(60) Provisional application No. 60/554,749, filed on Mar. 19, 2004.

(51) Int. Cl.
*A01H 5/00* (2006.01)

(52) U.S. Cl. ..... Plt./161

(58) Field of Classification Search ..... Plt./161
See application file for complete search history.

*Primary Examiner*—Anne Marie Grunberg
*Assistant Examiner*—Annette H Para
(74) *Attorney, Agent, or Firm*—Stratton Ballew PLLC

(57) ABSTRACT

A new and distinct apple tree named 'Mahana Red Braeburn' is disclosed. The fruit of the new variety is notable for its high color as compared to the fruit of other known 'Braeburn' trees.

2 Drawing Sheets

Latin name of the genus and species of the plant claimed: *Malus Mill.*

Variety denomination: 'Mahana Red Braeburn'.

BACKGROUND OF THE VARIETY

'Mahana Red Braeburn' originated as a limb sport mutation on a 'Braeburn' (unpatented) apple tree in an established orchard at Nelson, New Zealand. 'Mahana Red Braeburn' was first asexually propagated by budding by the inventor in New Zealand, and later at East Wenatchee, Wash., USA, and has been shown to remain true to type over successive generations.

BRIEF SUMMARY OF THE VARIETY

'Mahana Red Braeburn' apple tree is similar to 'Braeburn' in many respects, but is particularly distinguishable from 'Braeburn' and other known varieties by its attractive, highly colored fruit.

BRIEF DESCRIPTION OF THE PHOTOGRAPH

DETAILED BOTANICAL DESCRIPTION

Figure 1:
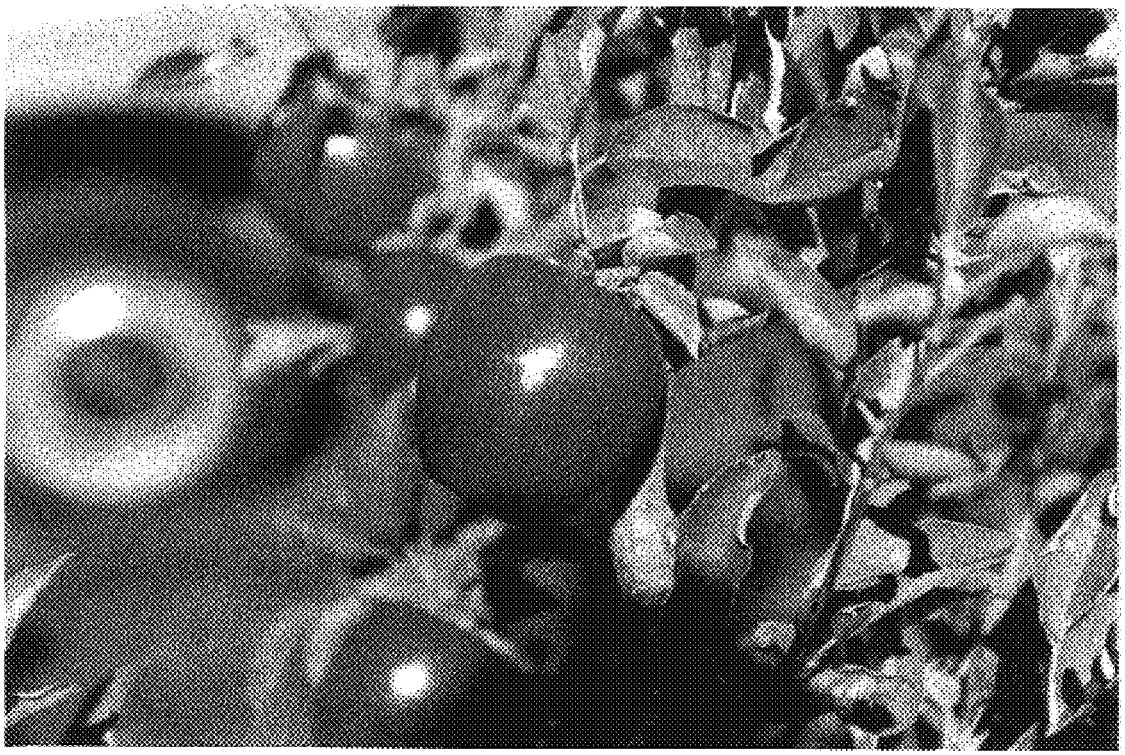
FIG. 1 shows the fruit and leaves of 'Mahana Red Braeburn'.
Figure 2:
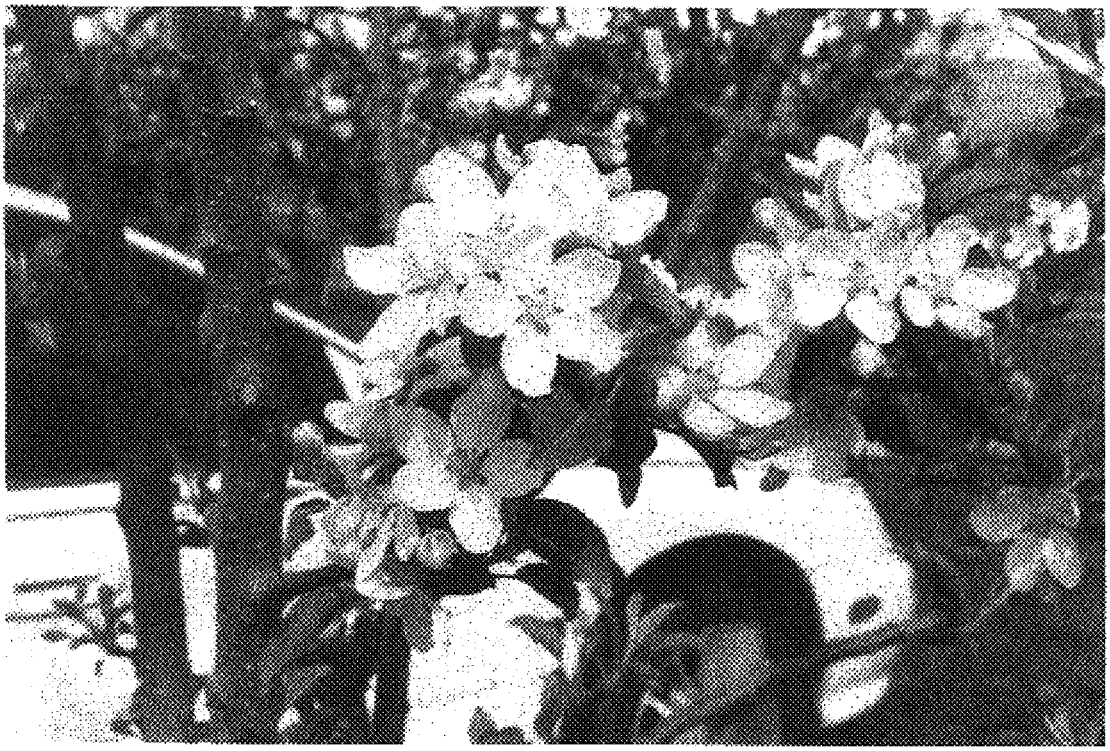
FIG. 2 shows the blossom, branches and leaves of 'Mahana Red Braeburn.'

The following is a detailed botanical description of the new and distinct variety of apple tree, based on observations of five year old specimens grown in New Zealand during the 1999 growing season, and Wenatchee, Wash., USA, during the 2004 growing season. All colors are described according to the Munsell Book of Colors. It should be understood that the botanical features described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Medium vigor; ramified; habit initially upright, becoming spreading to drooping; width 2.5 m; height 3.4 m; trunk diameter 10 cm at 30 cm above ground; bark smooth, becoming furrowed; color brown with grayish bloom (7.5 YR 3/6); lenticels elongated, tan (7.5 R 8/2), length 3.0 to 5.0 mm, width 1.0 to 2.0 mm.

Branch: 25 degree to 45 degree angle at emergence; size and texture typical of 'Braeburn' (not patented); mature branch diameter 5 cm at 20 cm from crotch of tree; color reddish brown (7.5 R 3/4), becoming brown (10 YR 4/4) on older wood.

One year old shoot: Upright; vigorous; length 30 to 80 cm; diameter 0.5 to 1.0 cm; Strong pubescence on upper half; length of internode avg. 2.6 cm; lenticels sparse, round, tan (7.5 R 8/2), diameter 0.5 mm, becoming more numerous on older wood.

Leaves: Length 6.5 to 8.5 cm, avg. 7.4 cm; width 4 to 5 cm, avg. 4.3 cm; Margin finely serrate to crenate; tip mostly acute; stipules small, length 5 to 8 mm, width 1 mm; leaf color grey green (5 GY 5/4); pubescence very fine, colorless; petiole length 2.2 to 3.5 cm, avg. 2.8 cm; petiole color grey green (10 GY 7/2); veins pale grey green (10 GY 7/2).

Flower: Medium size, diameter about 35 mm fully open; color of unopened flower at balloon stage, dark pink (7.5 R 3/10); color of fully open flower pure white on upper surface, lower surface retains pink color (5 R 4/12) near center of flower; petals oblong, touching, length 20 mm, width 8 mm; sepal length 6 mm, width 4 mm, color light green (2.5 GY 8/6), finely pubescent, arranged in a single row, average of 16 stames per flower; anthers light yellow (5Y 8.5/10); pistil has stigma curving slightly at distal end, club shaped, five styles fused at base approximately 10 mm in length; pollen light yellow (5Y 8.5/10); light fragrance not distinguishable from 'Braeburn'; First bloom April 12, full bloom April 17, petal fall April 27 (based on observations made during 2004 growing season in East Wenatchee, Wash., USA).

Fruit (based on observations made at mid harvest during 2001 growing season in East Wenatchee, Wash., USA):

*Size.*—Medium to large, diameter 7.5 to 8.0 cm, mass 290 g (compare to 'Joburn' U.S. Plant Pat. No. 11,992).

*Form.*—Oblong, symmetric; ribbing absent; slightly tapering at distal end, with inconspicuous lobes.

*Stem.*—Cavity width medium, 40 to 45 mm; depth medium, 15 mm, acute; basin cavity broad, 30 to 35 mm, shallow, 10 mm, obtuse; stem length 20 mm, width 2 mm, reddish green, colorless pubescence.

*Eye aperture.*—Slightly lobed, depth 1.0 cm, width 2.0 to 2.5.

*Locules.*—Medium size, quantity 5, open.

*Skin.*—Smooth, naturally glossy, no tendency to become greasy, not prone to russet, no tendency toward cracking in stem cavity, very thin.

*Lenticels.*—White, medium to numerous in density (5 to 15 per $cm^2$), round, more numerous toward apex, generally 1 mm or less in size.

*Color.*—General color effect bright red blush and stripe over 90 to 100% of fruit surface except around stem, where greenish ground color persists; ground color yellowish green (10 Y 6/8), primarily around stem cavity; over color bright pinkish red (10 RP 4/14); no russet observed; flesh color off white (7.5 Y 9/6).

*Texture.*—Very firm, crisp, juicy at prime maturity.

*Flavor.*—Sprightly subacid to acid, typical of 'Braeburn'; acidity high at harvest, up to 85%, decreasing with storage.

*Aroma.*—Typical for species.

*Core.*—Round, small, diameter 25 mm, length 28 mm; number of bundles ten; core lines indistinct; core open, calyx tube short, closed.

*Seed.*—Obovate, 2 per cell, color brown (10 YR 3/6), length 8 mm, width 4 mm, with loose adherence to carpel wall.

*Storage.*—Excellent, 6 to 8 months at 34 degrees F., 9 to 12 months in controlled atmosphere storage.

*Market use.*—Dessert and culinary.

Cold hardiness: No winter damage observed in Washington or New Zealand; similar to 'Braeburn.'

Disease resistance: Similar to 'Braeburn'; no special resistance noted.

What is claimed is:

1. A new and distinct apple tree substantially as described and illustrated herein.

* * * * *